United States Patent [19]
Jaeger

[11] Patent Number: 6,164,145
[45] Date of Patent: Dec. 26, 2000

[54] LIQUID SAMPLE AND METHOD

[76] Inventor: Ben E. Jaeger, 50 Hunter La., Bristol, Ill. 60512

[21] Appl. No.: 09/220,480

[22] Filed: Dec. 23, 1998

[51] Int. Cl.$^7$ ........................................... G01N 1/00
[52] U.S. Cl. ............................................ 73/863.83
[58] Field of Search ..................... 73/863.81–863.83, 73/863.85, 866.5

[56] References Cited

U.S. PATENT DOCUMENTS

| | | |
|---|---|---|
| 4,147,062 | 4/1979 | Jaeger . |
| 4,262,533 | 4/1981 | Jaeger . |
| 4,475,410 | 10/1984 | Jaeger . |
| 4,630,479 | 12/1986 | Wagener et al. ............... 73/863.83 |

*Primary Examiner*—Robert Raevis
*Attorney, Agent, or Firm*—Pyle & Piontek

[57] ABSTRACT

A sampling apparatus is characterized by a sampler coupled to a product-containing vessel by an adapter. The sampler has a bore received in the adapter and leading to an opening in the vessel. A plunger in the bore has an annular recess intermediate its ends. The plunger is reciprocated forward in the bore to project the recess through a forward outlet from the bore and through the vessel opening into the vessel to receive a sample of liquid therein. The plunger is then reciprocated rearward to retract the recess from the vessel and into the bore to a sample delivery point. When the plunger is in the sample delivery position, a relatively long portion of the sampler bore exists between the front of the plunger and the forward bore outlet. The sampler has two motors. A first one of the motors reciprocates the plunger during sampling cycles between its sample receiving and sample delivering positions. A second one of the motors operates when the sampler is idle to move the plunger to a parked position where its forward end is close to or at the forward outlet from the sampler bore. In its parked position, the plunger closes the forward outlet from the bore to prevent product from entering, stagnating in and clogging the forward end of the bore and thereby rendering the sampler inoperative.

24 Claims, 2 Drawing Sheets

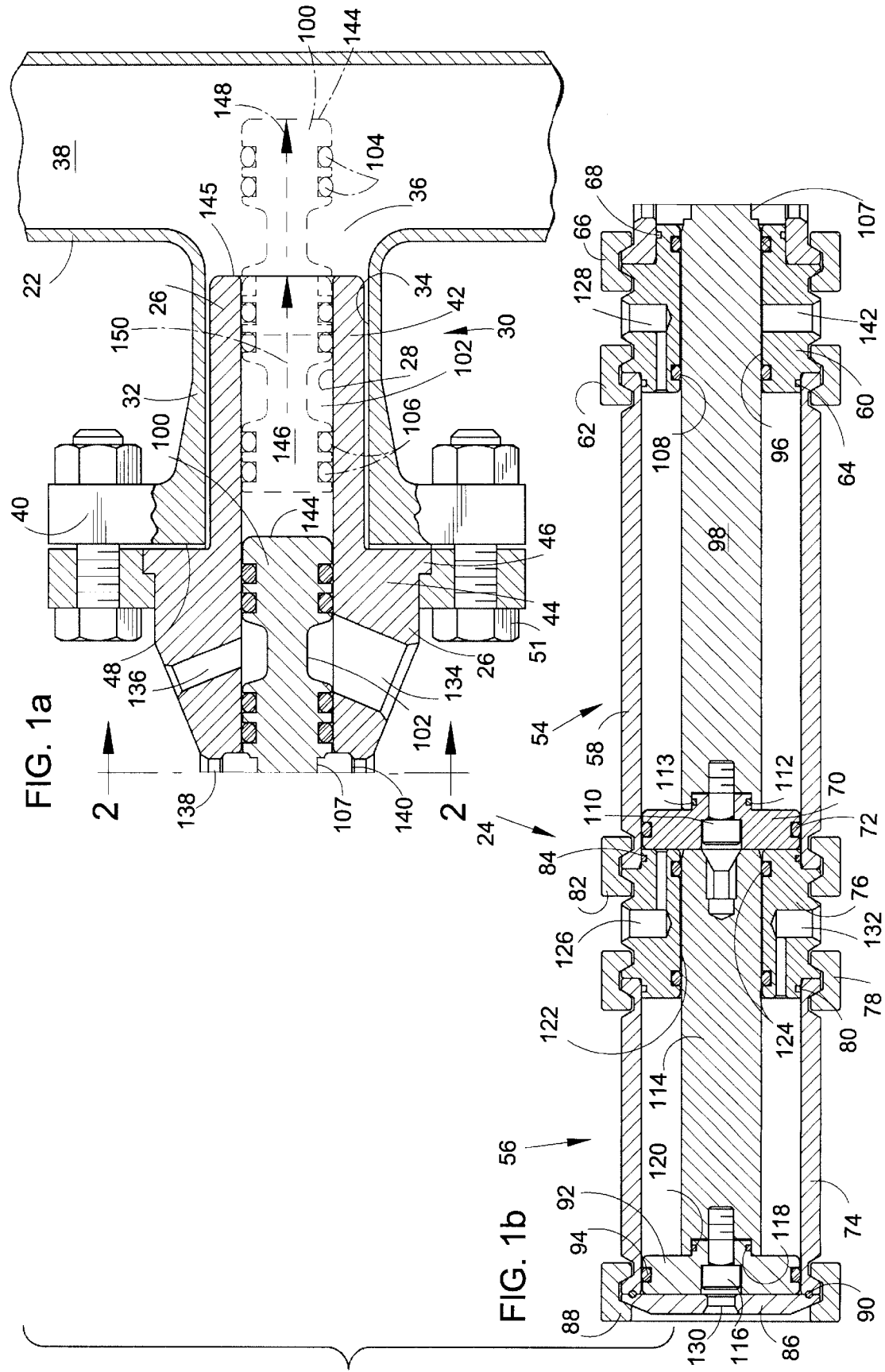

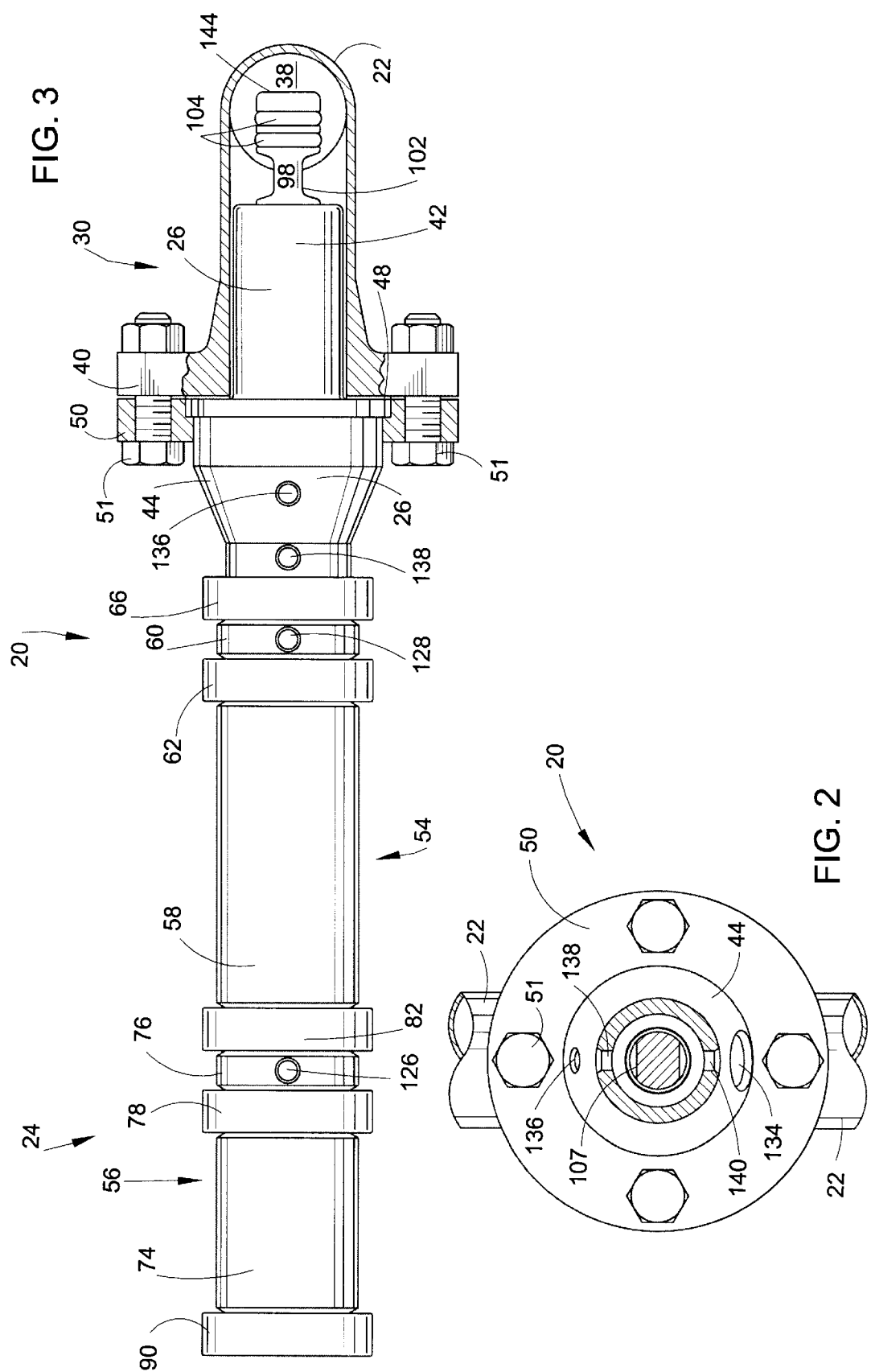

LIQUID SAMPLE AND METHOD

BACKGROUND OF THE INVENTION

The present invention relates to apparatus for extracting samples of liquid product from flow lines or tanks.

Certain manufacturing operations require that the immediate or overall composition of a liquid or fluid product flowing through a pipe or contained within a vessel or tank be monitored. Such monitoring ordinarily is accomplished with sampling apparatus, which takes samples of liquid from a main body of the liquid. Where a composite sample of the liquid is required, the sampler may be periodically operated to withdraw a series of small, measured amounts of the liquid as it passes a sampling point. The small, measured amounts are collected and admixed to form a representative sample of the total volume of liquid.

Other uses for samplers are in on-line analysis applications, in which the immediate composition of a liquid must be determined. For this application, the individual samples of liquid are not collected as a composite sample, but instead are received and analyzed separately.

Four exemplary types of sampling apparatus of the type contemplated by the prior art are disclosed in U.S. Pat. Nos. 4,147,062, 4,262,533, 4,475,410 and 4,744,255, issued to Ben E. Jaeger, the present inventor, and the teachings of all of which are incorporated herein by reference. Sampling apparatus of the type disclosed in said patents is attached to an access line or port to a pipe or vessel containing the body of liquid product, so that a liquid sample receiving recess in a plunger of the sampler can be extended through the line and an aperture in the pipe into the body of liquid for receiving a liquid sample in the recess. The plunger is then retracted to deliver the liquid sample to a collection point in the sampler.

The access line usually is attached to the pipe by a flange connected and sealed to the pipe around the aperture therein. The sampler includes, as described in said Jaeger patents, a body having a bore in which a plunger having a sample receiving recess is reciprocated. The bore communicates with the access line. The plunger is reciprocated to a sample receiving position in which the plunger recess is extended out of the body bore and into the pipe to receive a sample of the liquid product contained therein. The plunger is then reciprocated to a sample collecting position in which the plunger recess is retracted back into the bore to deliver the sample to a point in the bore where the sample is removed from the recess and collected.

It can happen that connecting the sampler to the pipe requires use of an access line having a relatively extended length. This can occur, for example, where the pipe is located such that an extended length access line is required in order to position the sampler in a serviceable position. Should the length of the access line be such that upon retraction of the plunger its forward end is positioned in the sampler bore considerably rearward or spaced from the forward outlet from the bore, then whenever and for as long as the plunger is retracted, a considerable length of the forward end of the sampler bore will be exposed to and fill with liquid product from the pipe. This is not a desirable situation, since when the plunger is retracted it is advantageous for the front of the plunger and any part of the sampler bore between it and the forward bore opening to be washed by the flow of product in the pipe. Should a considerable length of bore exist forward of the retracted plunger, the front of the plunger and the bore forward of it may be sufficiently removed from the main body of product so as to be exposed to stagnant product and not be continuously washed by the product. Product may then collect and congeal on the front of the plunger and in the bore forward of it, resulting in contamination of subsequent samples. It can also happen that product can accumulate in and clog the bore forward of the plunger, preventing reciprocation of the plunger and disabling the sampler. This condition is exacerbated by product of a type that is prone to clog when stagnant, such for example as product comprising paper pulp.

OBJECTS OF THE INVENTION

An object of the present invention is to provide a liquid sampler of the reciprocating plunger type, that is adapted to be coupled through a relatively long access line with product to be sampled, without occurrence of product clogging, forward of the plunger, in a sampler bore within which the plunger is reciprocated.

Another object is to provide such a sampler, wherein during idle sampler periods the length of the bore between a forward end of the plunger and a forward outlet from the bore is minimized.

A further object is to provide such a sampler in which the plunger is in a first position in the bore at the time of delivery of a product sample to a sample collection point and a second position during idle periods of the sampler.

Yet another object is to provide such a sampler wherein the plunger is at a third position in the bore during collection of a product sample from the main body of product.

SUMMARY OF THE INVENTION

In accordance with the present invention, there is provided a liquid sampling apparatus that includes a liquid sampler that is operable to obtain discrete samples of liquid from a body of liquid. The liquid sampler includes a sampler body having a bore with a forward opening, and plunger means in the sampler body bore has a liquid sample receiving aperture therein. Also included is motor means for reciprocating the plunger means in the bore to each of a sample receiving position where the aperture is extended out of the forward bore opening, a sample delivering position where the aperture is retracted to a position within the bore for collecting the sample, and a parked position within the bore and intermediate the sample receiving and delivering positions.

The plunger has a forward end that is rearward from the bore opening in the sample delivering position and at the bore forward opening in the parked position to close the opening to the bore and prevent entry into the bore of liquid from the body of liquid. The motor means includes first and second motor means. The second motor means comprises a piston in a cylinder and a piston rod having a rearward end attached to a forward end of the piston. The piston rod has a forward end that abuts and pushes the first motor means to move the first motor means in a direction to reciprocate the plunger means forward to the parked position. The first motor means, in torn, includes a piston in a cylinder. The first motor means is attached to a rearward end of the plunger means to reciprocate the plunger means in the sampler body bore. The second motor means is rearward from the first motor means and the forward end of the second motor means piston rod abuts a rearward side of the first motor means piston to push the first motor means piston in a direction to reciprocate the plunger means to the parked position.

The invention also contemplates a method of sampling a liquid product. The method comprises the steps of providing a sampler body having a longitudinal bore therein and a forward opening from the bore and positioning a plunger, having a sample collecting recess therein intermediate forward and rearward ends thereof, within the bore. Also included is the step of extending the plunger forward through the sampler body bore to a sample receiving position where the forward end of the plunger and the recess are projected out of the forward opening from the bore and into a body of liquid product to receive in the recess a sample of the product. There is then the step of retracting the plunger rearward through the sampler body bore opening and into the bore to deliver the plunger recess and sample therein to a sample collecting position in the bore. The forward end of the plunger, when the recess is at the sample collecting opening, is spaced rearward from the bore opening, so that a length of bore then exists between the plunger forward end and the opening from the bore. Next, there is the step of removing the sample from the recess at the sample collecting position, and then sequentially repeating the extending, retracting and removing steps until a desired number of samples have been delivered to the collecting position and removed from the recess. After the desired number of samples has been collected, the step is performed of moving the plunger to a parked position intermediate the sample receiving and collecting positions. The step of moving the plunger to the parked position comprises moving the plunger to position its forward end at the bore opening, so that the plunger closes the bore rearward of its forward end.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 is a cross-sectional side elevation view of the sampler, showing a sample receiving plunger of the sampler in each of its sample receiving, sample delivering and parked positions;

FIG. 2 is a side elevation view taken substantially along the lines 2—2 of FIG. 1, and FIG. 3 is a top plan view of a sampler according to the present invention.

DETAILED DESCRIPTION

The invention comprises a liquid product sampling apparatus having a sampling plunger that is reciprocated within a sampler body bore between the extremes of a liquid sample receiving position and a liquid sample collecting position. The plunger also is reciprocated to an idle or parked position, intermediate the sample receiving and collecting positions, whenever the sampler is to be idle. The sampling apparatus is adapted to be attached to an access line to a pipe or vessel containing a body of liquid product to be sampled. When so attached, the plunger is reciprocated forward and extended through an open forward end of the bore to position a sample receiving recess in the plunger within the body of liquid product to receive a sample of product in the recess. The plunger is then reciprocated rearward and retracted out of the body of liquid and back into the bore to move the recess and deliver the liquid sample therein to a sample collecting position within the sampler. The sampler is particularly adapted for use with an access line of sufficient length that the front of the plunger, when the plunger is in the sample delivering position, is sufficiently rearward of the forward opening from the sampler body bore that liquid product can enter, accumulate and stagnate in the bore forward of the plunger, if the plunger were to remain in the sample delivering position. Advantageously, the invention contemplates that the plunger be moved to an intermediate parked position when the sampler is idle. In the parked position the forward end of the plunger is closely adjacent to or at the forward opening from the bore. The plunger then closes the bore to entry of product that could otherwise accumulate, stagnate within and clog the bore.

Referring to the FIGS. 1 and 2, the sampler is indicated generally at 20 and includes a plunger having an annular recess that is extended into a pipe or vessel 22 for receiving in the recess a sample of liquid product from the pipe. The plunger is then retracted from the pipe to carry the liquid sample in the recess to a sample collection point. The recess is sized to receive and contain a precise volume of the liquid product and the sampler may be periodically actuated so that the liquid samples collected represent a composite sample of the liquid in the pipe. The plunger can be reciprocated by any suitable motor means, such as by a pneumatic motor means, indicated generally at 24, which as will later be described comprises two motor means. Seals on the plunger maintain a liquid seal between the interior of the pipe and the sample collection point, and between the sample collection point and the motor means, during reciprocation of the plunger. In this manner, the samples are generally insensitive to the pressure of the liquid in the pipe and the collected samples are protected against contamination.

More specifically, the sampler 20 has a body 26 with a longitudinal bore 28. An adapter 30 couples the sampler with liquid product in the interior of the pipe 22. The adapter has an elongate body portion 32 within which is a relatively long access line, port or passage 34. At its forward end the adapter body portion connects to the pipe around an opening 36 that provides communication with the interior 38 of the pipe and the liquid product therein. A circular flange 40 extends radially from a rearward end of the adapter body portion.

The sampler body 26 has an elongate cylindrical forward end 42. The sampler body also has an enlarged rearward end 44 and a radially extending flange 46 is at the juncture of the rearward and forward ends. To connect the sampler 20 to the adapter 30, the forward end 42 of the sampler body is extended into the adapter access line 34 to abut the sampler body flange 46 and the adapter flange 40, with an annular seal 48 positioned between the flanges. A collar 50 around the sampler body grips the flange 46 and a plurality of fasteners 51 extend through aligned passages in the collar and adapter flange 40 to attach the sampler to the adapter.

The motor means 24 for operating the sampler comprises a main motor means and a plunger assembly parking motor means, respectively indicated generally at 54 and 56. In the described embodiment, each motor means 54 and 56 is a pneumatic motor means, although other types of motor means could be used, such as electric or hydraulic motor means, depending upon the environment of the sampler. The motor means 54 comprises a cylinder 58, a forward end of which is removably attached to a rearward end of a head 60 by a quick release clamp 62 and sealed to the head by a seal 64. A forward end of the head is attached to a rearward end of the of the sampler body 26 by a quick release clamp 66 and sealed to the sampler body by a seal 68. A piston 70, carrying an annular seal 72 around its circumference, is slidable in the cylinder 58.

The motor means 56 comprises a cylinder 74, a forward end of which is removably attached to a rearward end of a head 76 by a quick release clamp 78 and sealed to the head by a seal 80. A forward end of the head 76 is removably attached to a rearward end of the motor means cylinder 58 by a quick release clamp 82 and sealed to the cylinder by a seal 84. A cap 86 is removably attached to the rearward end of the cylinder 74 by a quick release clamp 88 and sealed to the cylinder by a seal 90. A piston 92 having an annular seal 94 around its circumference is slidingly received in the cylinder 74.

A plunger assembly, indicated generally at 98, extends through the sampler body bore 28, through a bore 96 in the head 60 and into the cylinder 58 of the motor means 54. The plunger assembly includes a plunger 100 in which is an annular recess or sample receiving chamber 102 of predetermined volume. A pair of annular seals 104 is on the plunger forward of the sample chamber and a pair of annular seals 106 is on the plunger rearward of the sample chamber. Wrench flats 107 are on the plunger just rearward of the seals 106. From the wrench flats, the plunger extends rearward through a pair of annular seals 108 in the head bore 96 into the cylinder 58 of the motor means 54. At its rearward end the plunger is attached to the motor means piston 70 by a fastener 110. A cylindrical boss 112 on a forward side of the piston is closely received in a cylindrical recess 113 in a rearward end of the plunger assembly to maintain axial alignment of the piston and plunger.

The motor means 56 includes the piston 92, which is attached on its forward side to a rearward end of a piston rod 114 by a fastener 116. A cylindrical boss 118 on the piston is closely received in a cylindrical recess 120 in the piston rod to maintain axial alignment between the two. At its forward end the piston rod passes through a bore 122 in the head 76, within which a pair of annular seals 124 seals it to the head. At its very forward end the piston rod 114 is adapted to abut and push, but is not attached to, the rearward side of the piston 70.

The piston 70 and plunger assembly 98 are urged forward by introduction of air under pressure at an air inlet 126 in the head 76 and are urged rearward by introduction of air under pressure at an air inlet 128 in the head 60. In turn, the piston 92 and piston rod 114 are urged forward by introduction of air under pressure at an air inlet 130 in the cap 86 and are urged rearward by introduction of air under pressure at an air inlet 132 in the head 76. A sample discharge or outlet port 134 and an expelling fluid inlet port 136 are diametrically opposed in the enlarged rearward end 46 of the sampler body 26 at the sample delivery position within the bore 28. Diametrically opposed ports 138 and 140 are in the sampler body rearward of the ports 134 and 136, and a port 142 is in the head 60 in communication with the head bore 96.

The plunger assembly 98 is of a slightly smaller diameter than the diameter of the bores 28 and 96 within which it reciprocates. In consequence, the seals 104 and 106 carried by the plunger assembly, and the seals 108 within the head 60, control the concentricity of the plunger assembly within the bores and function as bearings to enable the plunger assembly to reciprocate easily. This prevents direct sliding contact between the relatively hard components of the sampler, whereby the life of the sampler is extended and its repair frequency reduced. The seals 104 and 106 also maintain a liquid seal between the inlet and outlet ports 136 and 134 and the liquid in the pipe 22. In addition, the seals wipe the bore 28 clean of sampled liquid with each reciprocation of the plunger assembly.

In operation of the sampler 20, and beginning with the sampler 20 in the condition shown in FIG. 1, to collect one or more samples of product from the line 22, pressurized air is applied to the air inlet 126. This drives the piston 70 and plunger assembly 98 rightward or forward to move the annular sample chamber 102 through the sampler body bore 28 and pipe opening 36 into the interior of the pipe to the sampling position, whereat the forward end of the plunger is located as indicated by the head of an arrow 148. Upon forward movement of the plunger assembly to extend the sample chamber into the liquid product in the pipe, the seals 106 move from behind the ports 134 and 136 to adjacent the front of the sampler body bore to wipe the bore forward of the ports. In this manner, the sampler body bore is cleaned of any accumulated liquid with each reciprocation of the plunger assembly.

As the plunger assembly 98 is extended, the plunger seals 106 form a liquid seal with the sampler body bore 28 forward of the inlet and outlet ports 136 and 134 before the plunger seals 104 move out of the bore. Similarly, upon leftward movement and retraction of the plunger assembly, the seals 104 enter the bore before the seals 106 move over and expose the ports. In consequence, a liquid seal is at all times maintained between the liquid in the pipe 22 and the inlet and outlet ports, and only the liquid sample received in the sample chamber 102 ever reaches the ports.

Upon extending the plunger assembly 98 forward to obtain a sample of liquid product, the sample chamber 102 is projected into the pipe 22 and exposed to the stream of liquid flowing through the pipe. The sample chamber is therefore washed by the product stream upon each cycle of operation of the sampler. This minimizes an accumulation of product in the chamber, and the annular shape of the chamber and its direct exposure to the product stream help prevent it from becoming clogged by solids. The sample collecting chamber is therefore self-cleaning of debris that may be encountered in product lines, so that when it is withdrawn into the sampler bore 28, it will carry a true sample of the liquid flowing through the pipe.

Upon the plunger assembly being fully retracted, the annular recess or sample chamber 102 is positioned at the sample discharge or outlet port 134. The liquid product sample in the sample chamber then passes through the sample discharge port for immediate analysis or collection, for example by being discharged into a sample collection container (not shown). To facilitate removal of the sample from the recess in the case of high viscosity or thixotropic materials, a stream of air or other sample compatible fluid can be introduced through the inlet port 136 to flush or blow the sample from the sample chamber in the plunger assembly. Alternatively, vacuum can be applied to the discharge port. The particular expelling fluid applied at the inlet port depends on the nature of the product sampled. Should the product sample require dilution for subsequent analysis, the expelling fluid may comprise the necessary diluent.

The samplers of said aforementioned Ben E. Jaeger patents are configured such that upon retraction of the plunger assembly to deliver a product sample to a collection point, a front end of the plunger is positioned relatively close to or at the outlet from the sampler bore within which the plunger reciprocates. Thus, the front of the plunger closes the bore to prevent liquid product from entering the bore.

Unlike the samplers of said Jaeger patents, the sampler 20 is adapted for use in situations where a sampler cannot be located relatively close to a product line. For such situations, the cylindrical body 32 of the adapter 30 and its access line 34 have a relatively long length to gain access to the pipe. The forward end 42 of the sampler body 26 that extends into the access line also is relatively long. In consequence, when the plunger assembly 98 is retracted to deliver a product sample in the recess 102 to the collection point at the discharge port 134, a forward end 144 of the plunger assembly is a considerable distance rearward from a forward outlet opening 145 from the sampler bore 28. In this position of the plunger assembly, a relatively long portion of the sampler bore, indicated generally at 146, then exists between the front of the plunger assembly and the sampler bore outlet. Product from the line 22 enters the bore portion 146, and because of the depth of the portion, the product tends to stagnate. If the product is thin and generally particulate free, stagnation within the bore portion may not present a problem, even if the sampler is idle for a relatively long time between sampling cycles. However, should the product be of a type that is prone to congeal, such as a viscous paper pulp product, it can harden within and clog the front portion of the bore if it is allowed to stagnate within the portion for a sufficiently long time.

To prevent product clogging within the forward sampler bore portion 146 when the sampler is idle, according to the present invention the motor means 24 includes the second motor means 56. Unlike prior samplers of the general type which do not have such a second motor means, the motor means 56 moves the plunger assembly 98 to a parked position when the sampler is to be idle. Movement of the plunger assembly to the parked position, as shown in FIG. 1, places the front end 144 of the plunger at the forward opening 145 from the sampler body bore 28, as indicated by the head of an arrow 150. The plunger then occupies the space within the bore portion 146 and closes the forward opening to the bore, whereby entry of product into the bore is prevented. Thus, with the plunger moved to its parked position, the sampler bore is closed to entry of product and the sampler can remain idle for as long as desired without its bore becoming clogged with product.

The sampler parking motor means 56 includes the piston 92 and piston rod 114. The forward end of the piston rod can push against but is not attached to the rearward side of the piston 70. To urge the piston 92 forward, air under pressure is introduced at the air inlet 130. With the sampler plunger assembly 98 in its fully retracted position, rightward movement of the piston 92 and its piston rod 114 pushes against the piston 70 to move the plunger assembly forward. The length of the stroke of the motor means 56, as determined by the distance the piston 92 travels between the cap 86 and the head 76, is just sufficient to move the plunger assembly to its parked position. Thus, whenever the sampler is to be idle, the motor means 56 is energized and the plunger assembly is moved to its parked position.

When the sampler 20 is to be actively sampling under control of the main motor means 54, the parking motor means 56 is brought to its retracted rearward idle position by application of air under pressure at the air inlet 132, so as not to interfere with the sampling operation. Then, when the present sampling cycle is over and the sampler 20 is to be idle, the motor means 56 is energized by application of air under pressure at the air inlet 130 to push the sampler plunger assembly 98 to its parked position. During the period that the plunger assembly is parked, the motor means 56 remains energized, by the continued application of air under pressure at the inlet 130, to resist rearward movement of the plunger assembly under the urging of the pressure of product acting on its forward end 144.

When sampling is to resume, pressurized air is removed from the inlet 130 and applied to the inlet 132 to retract the motor means 56. The sampler plunger assembly 98 may or may not try to follow the motor means 56 back as a result of the pressure of product acting on its forward end 144. In any event, pressurized air is applied to the air inlet 126 to move the plunger assembly forward, as indicated by the head of the arrow 148, and extend its sample receiving recess 102 into the product line 22 to receive a sample of liquid product therein. Air under pressure is then removed from the air inlet 126 and applied to the air inlet 128 to retract the plunger assembly and deliver the sample to the collection point at the sample outlet port 134. Sampling cycles then proceed as above described for as long as desired. When sampling is over and the sampler is to again be idle, pressurized air is removed from the inlets 126, 128 and 132 and the motor means 56 is actuated by pressurized air at the inlet 130 to move the plunger assembly to its parked position.

The ports 138 and 140 provide specific advantages in monitoring the need for maintenance of the sampler. With the port 138 closed and the port 140 open, product dripping out of the port 140 provides a visual indication of a need to replace the plunger seals106. If desired, a sensor can be placed in the port 140 to sense any leakage of product and signal the need to replace the plunger seals. Use of a sensor is particularly advantageous if leakage of product from the sampler were highly undesirable, such as where the product is an insecticide or radioactive. Alternatively, fluid may periodically be introduced at the port 138 to remove any product from around the plunger between the ports 138 and 140 and carry it to a sensor in the port 140 for detection.

The port 142 also serves the purpose of monitoring sampler seal integrity by providing a means to check the integrity of the seals 108 on its opposite sides. If the fluid used to operate the motor means 54 comes out of the port, that is an indication that the rearward seal 108 is worn. Should product exit the port, that indicates that the forward seal 108 requires replacement. Leakage of product out of the port 142 also indicates that the port 140 is plugged and/or is not being properly monitored.

The invention therefore provides an improved liquid sampler that is adapted for use in sampling product that has a tendency to congeal when stagnant, in situations where the sampler cannot itself be positioned closely adjacent to the pipe or vessel from which the product sample is obtained.

While one embodiment of the invention has been described in detail, various modifications and other embodiments thereof can be devised by one skilled in the art without departing from the spirit and scope of the invention, as defined in the accompanying claims.

What is claimed is:

1. A sampling apparatus, comprising:

a liquid sampler operable to obtain discrete samples of liquid from a body of liquid, said liquid sampler including a sampler body having a bore with a forward opening;

plunger means in said sampler body bore, said plunger means having a liquid sample receiving aperture therein, and motor means for reciprocating said plunger means in said bore to each of a sample receiving position where said aperture is extended out of said forward bore opening, a sample delivering position where said aperture is retracted to a position within said bore for collecting the sample, and a parked position within said bore and intermediate said sample receiving and delivering positions, said motor means including first and second motor means and said second motor means comprising a piston in a cylinder and a piston rod having a rearward end attached to a forward end of said piston, said piston rod having a forward end that abuts and pushes said first motor means to move said first motor means in a direction to reciprocate said plunger means forward to said parked position.

2. Sampling apparatus as in claim 1, wherein said plunger means has a forward end that is rearward from said bore opening in said sample delivering position and positioned close to said bore opening in said parked position.

3. Sampling apparatus as in claim 1, wherein said plunger means has a forward end that is rearward from said bore opening in said sample delivering position and at said bore forward opening in said parked position.

4. Sampling apparatus as in claim 1, wherein said plunger means aperture comprises an annular recess in and circumferentially around said plunger means, and including seal means for maintaining a seal between said bore opening and said sample delivering position during reciprocation of said plunger means.

5. Sampling apparatus as in claim 1, wherein said motor means reciprocates said plunger means between said sample receiving and delivering positions, and said second motor means moves said plunger means to said parked position.

6. Sampling apparatus as in claim 1, wherein said first and second motor means comprise pneumatic motor means.

7. Sampling apparatus as in claim 1, wherein said first motor means reciprocates said plunger means in each of said plunger means extension and retraction directions and said second motor means reciprocates said plunger means only in said plunger means extension direction.

8. A sampling apparatus, comprising:
   a liquid sampler operable to obtain discrete samples of liquid from a body of liquid, said liquid sampler including a sampler body having a bore with a forward opening;
   plunger means in said sampler body bore, said plunger means having a liquid sample receiving aperture therein, and
   motor means for reciprocating said plunger means in said bore to each of a sample receiving position where said aperture is extended out of said forward bore opening, a sample delivering position where said aperture is retracted to a position within said bore for collecting the sample, and a parked position within said bore and intermediate said sample receiving and delivering positions,
   wherein said motor means includes first and second motor means and said second motor means moves said first motor means and said plunger means to extend said plunger means in a forward direction to said parked position.

9. Sampling apparatus as in claim 8, wherein said second motor means comprises pneumatic motor means including a piston in a cylinder and attached to a rearward end of said plunger means to reciprocate said plunger means between said sample receiving and delivering positions.

10. Sampling apparatus as in claim 8, wherein said second motor means comprises a piston in a cylinder and a piston rod having a rearward end attached to a forward end of said piston, said piston rod having a forward end that abuts and pushes said first motor means to move said first motor means in a direction to reciprocate said plunger means forward to said parked position.

11. Sampling apparatus as in claim 10, wherein said first motor means includes a piston in a cylinder and is attached to a rearward end of said plunger means to reciprocate said plunger means in said sampler body bore, said second motor means is rearward of said first motor means and said forward end of said second motor means piston rod abuts a rearward side of said first motor means piston to push said first motor means piston in a direction to reciprocate said plunger means to said parked position.

12. Sampling apparatus as in claim 11, wherein said first motor means piston rod and said plunger means are axially aligned.

13. A sampling apparatus for obtaining discrete samples of liquid product from a body of liquid product, comprising:
   a sampler body having a bore extending therethrough and a forward opening from said bore;
   a sampling plunger received in said bore, said plunger having a liquid sample receiving recess therein intermediate forward and rearward ends thereof, and
   motor means for reciprocating said plunger in said bore in a forward direction to extend said forward end of said plunger and said recess through said forward bore opening into the body of liquid product to receive a sample of the product in said recess, for reciprocating said plunger in said bore in a rearward direction to retract said forward plunger end and said recess through said bore opening and said bore to a sample collecting position within said bore, and for reciprocating said plunger to a parked position forward from said sample collecting position and rearward from said sample receiving and collecting position, wherein said motor means comprises first and second motor means and said first motor means comprises pneumatic motor means having a piston coupled to a rearward end of said plunger for reciprocating said plunger in said bore between said sample collecting and receiving positions, and said second motor means comprises pneumatic motor means having a piston coupled to said first motor means piston and said plunger for moving said first motor means piston and said plunger to move said plunger to said parked position.

14. A sampling apparatus as in claim 13, wherein said second motor means includes a piston rod having a rearward end coupled to said second motor means piston and a forward end that is move by said second motor means piston against said first motor means piston to push said first motor means piston to move said plunger to said parked position.

15. A sampling apparatus as in claim 14, wherein said second motor means is rearward from said first motor means and said second motor means piston rod and said plunger are coaxial.

16. A sampling apparatus as in claim 13, including means in said sampler body bore at said sample collecting point for receiving the liquid sample from said recess.

17. A sampling apparatus as in claim 13, including seal means on said plunger on opposite sides of said recess for maintaining a liquid seal between the body of liquid product and said sample collection point during operation of said liquid sampler.

18. A sampling apparatus as in claim 13, wherein said first motor means reciprocates said plunger between said sample receiving and collecting positions, and said second motor means moves said first motor means to reciprocate said plunger to said parked position.

19. A sampling apparatus as in claim 13, wherein said forward end of said plunger, when said plunger is in said sample collecting position, is spaced rearward from said bore opening.

20. A sampling apparatus as in claim 19, wherein said forward end of said plunger, when said plunger is in said parked position, is forward of said forward end when said plunger is in said sample collecting position and close to said bore forward opening, said plunger closing said bore rearward of said forward end of said plunger.

21. A sampling apparatus as in claim 19, wherein said forward end of said plunger, when said plunger is in said parked position, is at said bore opening.

22. A method of sampling a liquid product, comprising the steps of:
   providing a sampler body having a longitudinal bore therein and a forward opening from the bore;
   positioning a plunger, having a sample collecting recess therein intermediate forward and rearward ends thereof, within the bore;
   extending the plunger forward through the sampler body bore to a sample receiving position where the forward end of the plunger and the recess are projected out of the forward opening from the bore and into a body of liquid product to receive in the recess a sample of the product;
   after said extending step, retracting the plunger rearward through the sampler body bore opening and into the bore to deliver the plunger recess and sample therein to a sample collecting position in the bore, the forward end of the plunger, when the recess is at the sample collecting opening, being spaced rearward from the bore opening, so that a length of bore then exists between the plunger forward end and the opening from the bore;
   removing the sample from the recess at the sample collecting position;
   sequentially repeating said extending, retracting and removing steps until a desired number of samples have been delivered to the collecting point and removed from the recess, and
   after the desired number of samples have been collected, moving the plunger to a parked position intermediate the sample receiving and collecting positions,
   wherein said plunger extending and plunger retracting steps are performed using respective first and second plunger moving motors.

23. A method as in claim 22, wherein said moving step comprises moving the plunger to position its forward end close to the bore opening, so that the plunger closes the bore rearward of its forward end.

24. The method as in claim 22, wherein said moving step comprises moving the plunger to position its forward end at the bore opening, so that the plunger closes the bore rearward of its forward end.

* * * * *

UNITED STATES PATENT AND TRADEMARK OFFICE
CERTIFICATE OF CORRECTION

PATENT NO. : 6,164,145
DATED : December 26, 2000
INVENTOR(S) : Ben E. Jaeger

Page 1 of 1

It is certified that error appears in the above-identified patent and that said Letters Patent is hereby corrected as shown below:

Column 9,
Line 19, after "said" insert -- first --
Line 51, "second" should be -- first --

Column 10,
Line 5, "first" should be -- second --

Signed and Sealed this

Twenty-third Day of October, 2001

Attest:

*Nicholas P. Godici*

Attesting Officer

NICHOLAS P. GODICI
*Acting Director of the United States Patent and Trademark Office*